United States Patent
Iyriboz et al.

(12)

(10) Patent No.: US 6,369,812 B1
(45) Date of Patent: *Apr. 9, 2002

(54) INTER-ACTIVE VIEWING SYSTEM FOR GENERATING VIRTUAL ENDOSCOPY STUDIES OF MEDICAL DIAGNOSTIC DATA WITH A CONTINUOUS SEQUENCE OF SPHERICAL PANORAMIC VIEWS AND VIEWING THE STUDIES OVER NETWORKS

(75) Inventors: Tunc A. Iyriboz, Hershey, PA (US); Timothy R. Carroll, Cleveland Heights, OH (US)

(73) Assignee: Philips Medical Systems, (Cleveland), Inc., Highland Heights, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/980,169

(22) Filed: Nov. 26, 1997

(51) Int. Cl.[7] .............................................. G06T 15/00
(52) U.S. Cl. ........................ 345/419; 345/427; 382/128
(58) Field of Search ........................ 364/413.22, 413.24, 364/413.19, 413.13; 345/419, 427; 382/128

(56) References Cited

U.S. PATENT DOCUMENTS

| | | | |
|---|---|---|---|
| 4,710,876 A | 12/1987 | Cline et al. | 364/414 |
| 4,719,585 A | 1/1988 | Cline et al. | 364/518 |
| 4,751,643 A | 6/1988 | Lorensen et al. | 364/414 |

(List continued on next page.)

OTHER PUBLICATIONS

Chen, S.E. Quicktime VR—An Image–Based Approach to Virtual Environment Navigation SIGGRAPH '95. Proceedings of the 22nd Annual ACM conference on Computer Graphics. pp. 29–38, 1995.*

(List continued on next page.)

*Primary Examiner*—Mark Zimmerman
*Assistant Examiner*—Philip H. Stevenson
(74) *Attorney, Agent, or Firm*—Fay, Sharpe, Fagan, Minnich & McKee, LLP

(57) ABSTRACT

An interactive virtual endoscopy system 10 includes a CT scanner 12 or other non-invasive examination apparatus which examines an interior region of a subject 14 in an examination region 16 and generates data indicative thereof. The data is stored in a volume image data memory 20. Using a sequence generating computer 22, a human operator 24 generates a sequence of sphere-mappable panoramic views of selected portions of the CT data along a viewpath in the patient 14. The sequence generating computer includes a view renderer 182 for rendering a plurality of views which in total cover the entire visual space about a viewpoint on the viewpath within the subject. A view compositer 240 combines the plurality of views into a full image covering the entire visual space about the viewpoint. The sequence is transferred to a server 26 which processes the data and makes it available for remote access. Over a local area network (LAN) 30, the data is selectively transferred, based on the commands of a remote human viewer 32, to a remote viewing computer 34. The data in decompressed and mapped into a spherical image for display on a remote display screen 36.

Viewers of the sequence of spherical images have the liberty to turn at will and view in any direction from a particular viewpoint instead of being constrained to a look-forward path. In this way, viewers retain the sense of order and space which a look-forward series provides but with the added capability to investigate completely a space from any given viewpoint.

11 Claims, 12 Drawing Sheets

U.S. PATENT DOCUMENTS

| | | | |
|---|---|---|---|
| 4,882,679 A | | 11/1989 | Tuy et al. ............... 364/413.22 |
| 4,965,753 A | * | 10/1990 | Kraemer ...................... 345/427 |
| 4,998,165 A | | 3/1991 | Lindstrom .................... 358/81 |
| 5,079,699 A | | 1/1992 | Tuy et al. ............... 364/413.22 |
| 5,243,664 A | | 9/1993 | Tuy ............................... 382/6 |
| 5,261,404 A | | 11/1993 | Mick et al. .............. 128/653.1 |
| 5,283,837 A | | 2/1994 | Wood ............................ 382/6 |
| 5,297,043 A | | 3/1994 | Tuy et al. .................... 364/422 |
| 5,297,551 A | | 3/1994 | Margosian et al. ...... 128/653.2 |
| 5,371,778 A | | 12/1994 | Yanof et al. ........... 364/413.22 |
| 5,396,583 A | * | 3/1995 | Chen et al. ................. 345/429 |
| 5,412,763 A | | 5/1995 | Knoplioch et al. ......... 395/124 |
| 5,432,895 A | | 7/1995 | Myers ........................ 395/119 |
| 5,552,605 A | | 9/1996 | Arata .................... 250/363.04 |
| 5,594,844 A | | 1/1997 | Sakai et al. ................. 395/127 |
| 5,611,025 A | | 3/1997 | Lorensen et al. ........... 395/119 |
| 6,232,977 B1 | * | 5/2001 | Chen .......................... 345/425 |

OTHER PUBLICATIONS

Heid. J. "VR:Quicktime's New Edge." MacWorld. Jul., 1995. pp. 98–103.*

Virtual Voyage: Interactive Navigation in the Human Colon. Computer Graphics (SIGGRAPH '97) Proceedings. pp. 27–34. Aug. 8, 1997.*

Mori, et al. "Virtualized Endoscope System—An Application of Virtual Reality Technology to Diagnostic Aid" IEICE Trans. on Inf. & Syst. vol #79–D, No. 6, Jun. 1996 pp 809–819 (XP000595187).

Chen, "QuickTime VR—An Image–Based Approach to Virtual Environment Navigation", Computer Graphics Proceedings, Los Angeles Aug. 6–11, 1995 pp. 29–38 (XP000546213).

Wilcox, Sue. "Extending VRML With Real Space Combining Panoramas with VRML." Web Techniques, Mar. 1997.

* cited by examiner

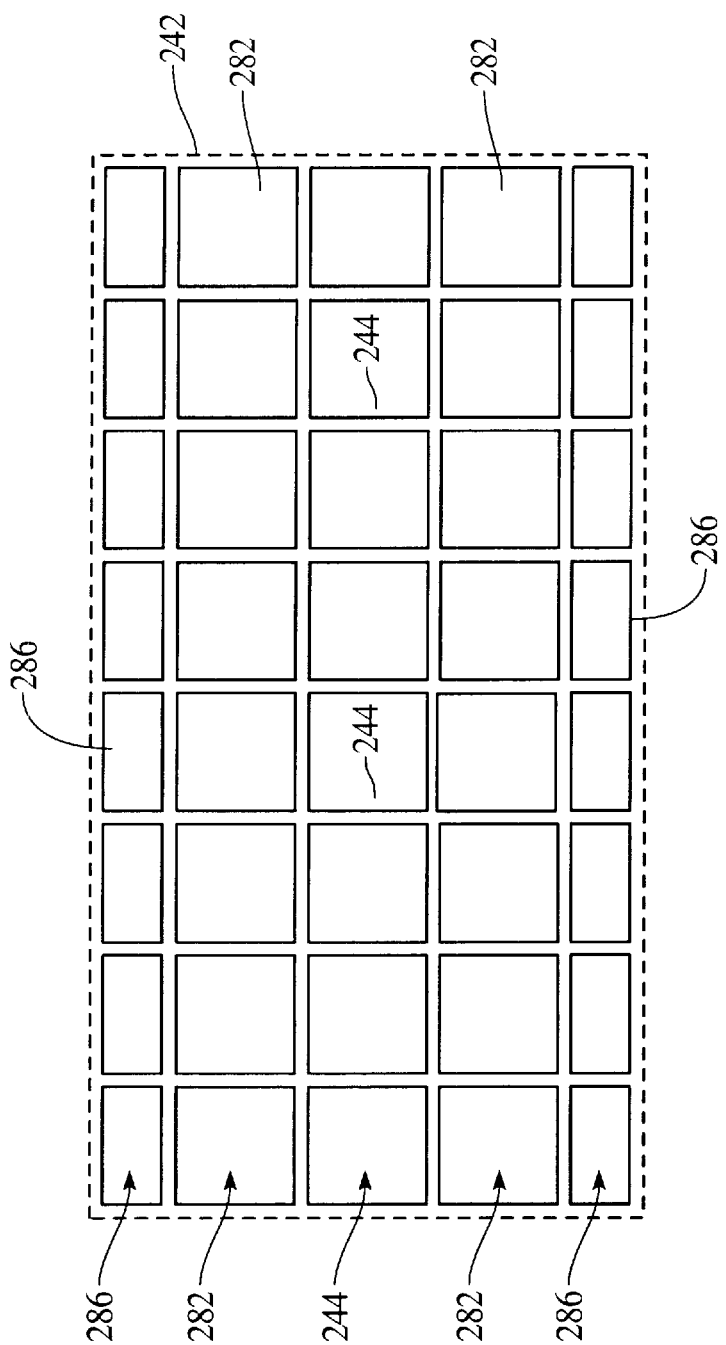

INTER-ACTIVE VIEWING SYSTEM FOR GENERATING VIRTUAL ENDOSCOPY STUDIES OF MEDICAL DIAGNOSTIC DATA WITH A CONTINUOUS SEQUENCE OF SPHERICAL PANORAMIC VIEWS AND VIEWING THE STUDIES OVER NETWORKS

BACKGROUND OF THE INVENTION

The present invention relates to the image display arts. It finds particular application in conjunction with providing three-dimensional presentations of diagnostic medical images on remote video monitors and will be described with particular reference thereto. In particular, the invention relates to interactive visualization of internal cavities in an organism, such as the intestines, bronchi, arteries and the like. However, it is to be appreciated that the invention finds application to other areas, such as virtual viewing of internal cavities of non-organic subjects such as pipes and sealed vessels. In addition, it will be appreciated that the invention has broader application in conjunction with generating three-dimensional diagnostic images from data acquired from other imaging modalities, e.g., by magnetic resonance imaging and ultrasound.

Heretofore, an endoscope is used to view passages through or the interior of organs such as the bronchi, esophagus, stomach, etc. The endoscope is threaded into internal cavities within the human body to provide real-time, high resolution views of the interior. The views may be recorded on video tape for later viewing. Further, the video images may be electronically transmitted to remote locations. However, there are a number of disadvantages with endoscopic examinations and video recordings thereof. The endoscope provides the operator and remote viewers with only a limited field of view without the ability to review in a reverse direction. Another problem with endoscopic examination is that it is not capable of being used with cavities that do not have an opening to the outside. In this regard, where possible, certain cavities must be surgically perforated to allow access to the endoscope. Further, because endoscopic examination can be uncomfortable or even painful, the procedure requires some sedation or anesthesia to reduce patient discomfort.

The use of computed tomography (CT) scanners using X-rays also provides limited inspection of internal cavities. CT scanners irradiate the planar region of a subject from various angles and detect the intensity of radiation passing there through. From the angle and radiation intensity information, two dimensional image representations of the plane are reconstructed. A typical image representation includes a 512 by 512 pixel array, although smaller and larger arrays are known. In a black and white image, each pixel has a corresponding value or number which is indicative of the gray scale to be displayed at that pixel. For three-dimensional imaging, a plurality of slices are generated, e.g., 60 closely adjacent parallel slices, each of which is represented by a 512 by 512 array of pixel values. The pixel values of the multiple slices are treated as a 512 by 512 by 60 pixel array or three dimensions of image data. Various planes or other surfaces can be defined through the three dimensional data and displayed. However, visualizing the interior of a three dimensional cavity from a series of slices is difficult.

In effort to improve visualization, techniques have been developed for generating a three dimensional representation allowing the inspection of an object along any cutting plane. With these techniques, appropriate planes and surfaces may be selected which permit viewing of the internal surfaces of cavities in the human body. That is, a slice image may be generated through a length of the esophagus. Such a slice can be processed to reveal the internal surface of one-half of the internal cylindrical length of the organ. Generally, such three dimensional presentations include a display of only the extended surfaces which a viewer would see and an internal part of the object through the cut of the object by an appropriate plane or surface.

To generate the pixel values for display, every pixel value of the three dimensional data is examined. Each data value is examined to determine whether or not it shows in the resultant image. Each data value which does show is assessed relative to the other data values to determine what contribution, if any, it makes to the image. None can be readily dismissed as not showing. Specifically, air produces a pixel value characteristic of black. Because air is transparent to the viewer, values from pixels hidden behind pixels whose values are indicative of air show through, hence must be displayed. Analogously, other types of tissue that have characteristic pixel values or CT numbers are also defined as transparent and removed from the view. Hence, the location of the pixel within the data alone is not determinative of whether or not the pixel value would show in the image. Rather, each pixel value has to be considered in the context of its surrounding pixels. This is computationally very time-consuming. Note that a 512 by 512 by 60 pixel data set contains almost 16 million pixels. Various techniques have been developed, many of which are application-specific, i.e., for reducing or identifying a subset of all available pixels to project up to the cutting surface or viewing screen to determine their contributions.

To visualize depth, the angle of the tangent to the surface at each point is estimated and shading is added in accordance with the angle of the surface tangent relative to a preselected illumination point. In a black and white CT image, the shading is added by increasing the brightness to whiteness of each pixel value in proportion to how nearly perpendicular it is to the light source, and by increasing the black scale in proportion to the degree that the tangential surface faces away from the light source. For example, a gray scale value that is proportional to the sine/cosine of the angle between the tangent surface and the light source may be combined with each pixel value.

Once the three dimensional presentation is displayed on the screen, it is often advantageous to view it from a different orientation. For example, a critical surface portion may be partially obscured or it may be necessary to see the back side before starting surgery. For the new viewpoint, the entire process is repeated anew. Effectively, all of the data within the three dimensional volume is rotated to the appropriate orientation relative to the viewing screen, and the contribution of each pixel is projected up the plane of the screen for reassessment. All of the data is rotated or shifted to achieve the proper location of the screen relative to the data before the data was projected up to the screen. The shifting of almost 16 million pixels of data and the interpolation of data, where necessary, further adds to processing time.

Viewing the CT data with key-frame techniques provides yet another improvement in the visualization of internal cavities. In one key-frame technique, an operator uses software to move through the data and render images from a certain viewpoint and in a certain direction. The operator generates a series of such images which may then be viewed sequentially as an animation. Some of the problems with key-frame animation are the same as with the video recording of an endoscopy study. The secondary viewer has a limited field of view and is restricted to those key-frames selected by the initial operator. Further, such studies are overly large and cumbersome to use on networks.

Another technique to visualize internal cavities is forward-looking virtual endoscopy which is a type of key-frame animation. Using a software package, an operator selects a path within a cavity or passage. Sequential forward-looking views or key-frames are then generated along the path and displayed. Forward-looking virtual endoscopy also suffers from some of the same problems as actual endoscopy. That is, a secondary viewer is constrained to a limited field of view and only to forward-looking views. In addition, virtual endoscopy studies generate large amounts of data which tax network resources in their transmission, require significant time to download and require significant resources for their storage. In order to view a study prepared from a data set, an entire video sequence must first be downloaded before any image may be viewed. Data compression of a virtual endoscopy video can speed transmission and smooth playback over a network but it also degrades noticeably the quality of the images.

Forward-looking virtual endoscopy may be enhanced by capturing images outside of key-frame animation. In this technique, the radiologist leaves the key-frame animation paradigm of image capture to manually reorient for capture of structures which are, for example, perpendicular to a viewpath through an organ. This also has its problems. First, it is difficult and time-consuming to capture views while constructing a sequence of virtual endoscopy images. Second, some visio-spatial context of the organ is lost in the frequent reorientations necessary for adequate coverage of the organ structure and subsequent reorientations of the camera to recover the original path. Thus, there is a possibility that the radiologist charged with capturing sequences will not capture some views crucial to diagnostic confidence due to the difficulties inherent in manual navigation and capture of images in virtual endoscopy datasets and subsequent reorientations of the rendering camera. In particular, the back surfaces of structures blocking passages require special attention. Failure to capture fully and accurately the context of the structure is possible if capture is left entirely to manual camera orientation.

The present invention contemplates a new and improved method and apparatus for inter-active virtual endoscopy over networks which overcomes the above-mentioned problems and others.

SUMMARY OF THE INVENTION

In accordance with the present invention, a medical diagnostic apparatus presents a three dimensional image presentation on a two dimensional display. An image data memory for stores image data indicative of a three dimensional volume. An image data memory accessor selectively accesses the stored image data. A view renderer renders a plurality of views which in total cover the entire visual space about a viewpoint within the three dimensional volume. A view compositor combines the plurality of views into a full image covering the entire visual space about the viewpoint. A mapper maps the full image into a spherical, panoramic image. A video processor displays a portion of the spherical, panoramic image on the two dimensional display.

In accordance with a more limited aspect of the present invention, a pitch control controls the pitch of the displayed spherical panoramic image. A yaw control controls the yaw of the displayed spherical panoramic image. An environmental mapping processor controls the video processor to display other portions of the spherical, panoramic image in accordance with the pitch and yaw controls.

In accordance with another more limited aspect of the present invention, a server between the image data memory accessor and the view renderer permits remote display of the panoramic image on the two-dimensional display.

In accordance with another aspect of the present invention, a method of generating a three dimensional image presentation using a computer is provided. Image data is stored which is indicative of a three dimensional array of pixels. A viewpoint is selected within the three-dimensional array. A plurality of two-dimensional arrays is generated which in total cover the entire spherical space about the viewpoint At least one of the plurality of two-dimensional arrays is divided into a plurality of first polygon arrays. The plurality of first polygon arrays is scaled into a plurality of second polygon arrays. The plurality of second polygon arrays and a portion of the plurality of two-dimensional arrays are combined to form a full two-dimensional array covering the entire spherical space about the viewpoint. The full two-dimensional array is mapped into a spherical view. At least a portion of the mapped, full, two-dimensional array is displayed as image pixels in a human-readable display.

In accordance with a more limited aspect of the invention, the three dimensional array of pixels is generated through a medical diagnostic exam of a patient.

In accordance with a still more limited aspect of the invention, the plurality of two-dimensional arrays which in total cover the entire spherical space about the viewpoint is six. The first polygon arrays are triangular arrays. The second polygon arrays are rectangular arrays.

One advantage of the present invention is that it provides full, unobstructed spherical panoramic views from within a three-dimensional array of image data.

Another advantage of the present invention is that it facilitates remote viewing and diagnoses of internal cavities as represented in the three-dimensional array of image data, A further advantage of the present invention is that it permits greater diagnostic confidence for secondary viewers of the three-dimensional array of image data.

Still another advantage of the present invention is that it permits rapid transmission of the images to remote locations over networks and more efficient use of network resources.

Further, although an endoscope examination is mostly non-invasive, the procedure still requires some sedation or anesthesia to reduce patient discomfort.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components and in various steps and arrangement of steps. The drawings are only for purposes of illustrating a preferred embodiment and are not to be construed as limiting the invention.

FIG. 6B illustrates the arrangement of the 26 views of FIG. 5B to obtain a full, flat image for a low-distortion spherical panoramic view; and, FIG. 7 is a partial detailed diagrammatic illustration of a second embodiment of a portion of the sequence generating computer 22 of FIG. 1;

DETAILED DESCRIPTION OF THE PREFERRED EMBODIMENTS

Figure 1:
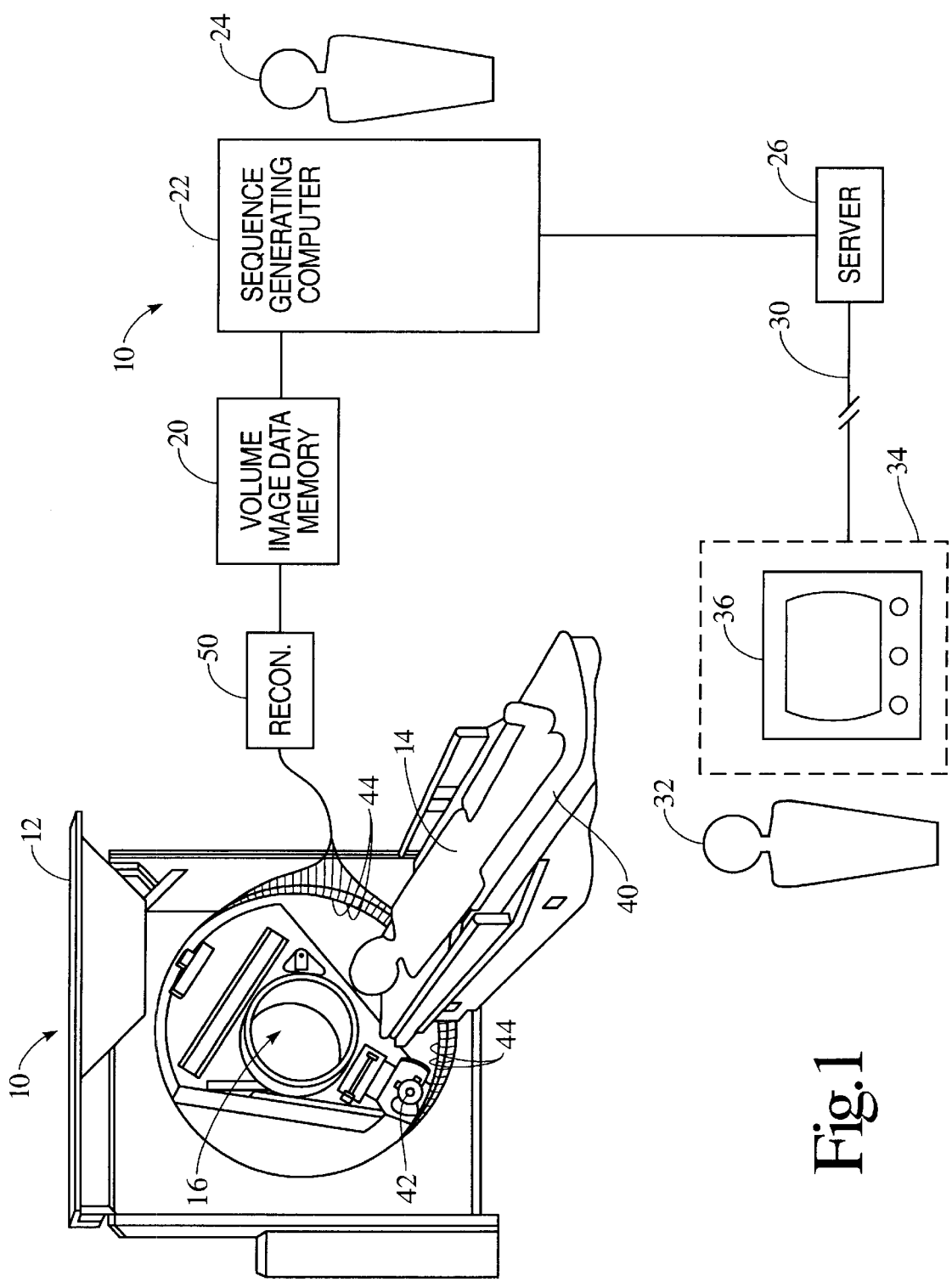
FIG. 1 is a diagrammatic illustration of an inter-active viewing system for generating virtual endoscopy studies of medical diagnostic data in accordance with the present invention.

With reference to FIG. 1, an interactive virtual endoscopy system 10 includes a CT scanner 12 or other non-invasive examination apparatus which examines an interior region of a subject 14 in an examination region 16 and generates data indicative thereof. The CT data is stored in a volume image data memory 20. Using a sequence generating computer 22, a human operator 24 generates a sequence of sphere-mappable panoramic views of selected portions of the CT data along a viewpath in the patient 14. The sequence is transferred to a server 26 which processes the data and makes it available for remote access. Over a local area network (LAN) 30, the data is selectively transferred, based on the commands of a remote human viewer 32, to a remote viewing computer 34 where the data is decompressed and displayed on a remote display screen 36.

With continuing reference to FIG. 1, more specifically, the CT scanner includes a subject support or patient couch 40 for supporting a patient or other subject received in the examination region 16. An irradiating means 42, such as an x-ray tube, irradiates the patient with x-rays or other penetrating radiation. A radiation receiving means, such as radiation detectors 44, receive diagnostically encoded radiation which has traversed the examination region. In the preferred embodiment, the x-ray tube generates a fan-shaped beam of x-rays. The fan-shaped beam of x-rays passes through the subject and impinges upon an arc of the radiation detectors 44. The x-ray tube is mounted for rotation by a motor or other rotating means around the examination region, such that the subject is irradiated from a multiplicity of directions. The radiation detectors are positioned either in a stationary ring surrounding the examination region or in an arc which rotates with the x-ray tube to receive the radiation which has traversed the subject. The patient is moved along a longitudinal axis of the CT scanner either continuously for spiral scanning or incrementally, to generate a multiplicity of slices. Optionally, a wider x-ray beam may be generated and a plurality of rows of detectors may be provided such that a plurality of slices are generated concurrently.

An image reconstruction processor 50 samples the radiation from the radiation detectors 46 and reconstructs an image representation therefrom. It will be noted, that each time a radiation detector 16 is sampled, the intensity of sampled radiation represents a sum of the radiation absorptive properties of tissue lying along a ray or path between the x-ray source (at the time of the sampling) and the sampled detector. Because the intensity of radiation at the x-ray source is known and the intensity of detected radiation is known, the line integral of the material in the region 16 can be estimated such that it represents the line integral of the radiation absorption or attenuation along each ray. The reconstruction processor 50 extrapolates or interpolates as necessary to generate CT numbers corresponding to each of a three dimensional array of voxels.

An original volume image data memory 20 stores the reconstructed volumetric data. Each of the CT numbers for the data can be conceptualized as being addressable by its coordinate location along three orthogonal axes, e.g. x, y, and z axes of the examined volume. For example, the pixel values may be triply subscripted variables, such that the corresponding pixel value is accessible based on its x, y, z spatial position in the volume. In this manner, pixel values representing a regular distribution over an imaged volumetric region are generated and stored.

Path Selection

Figure 2A:
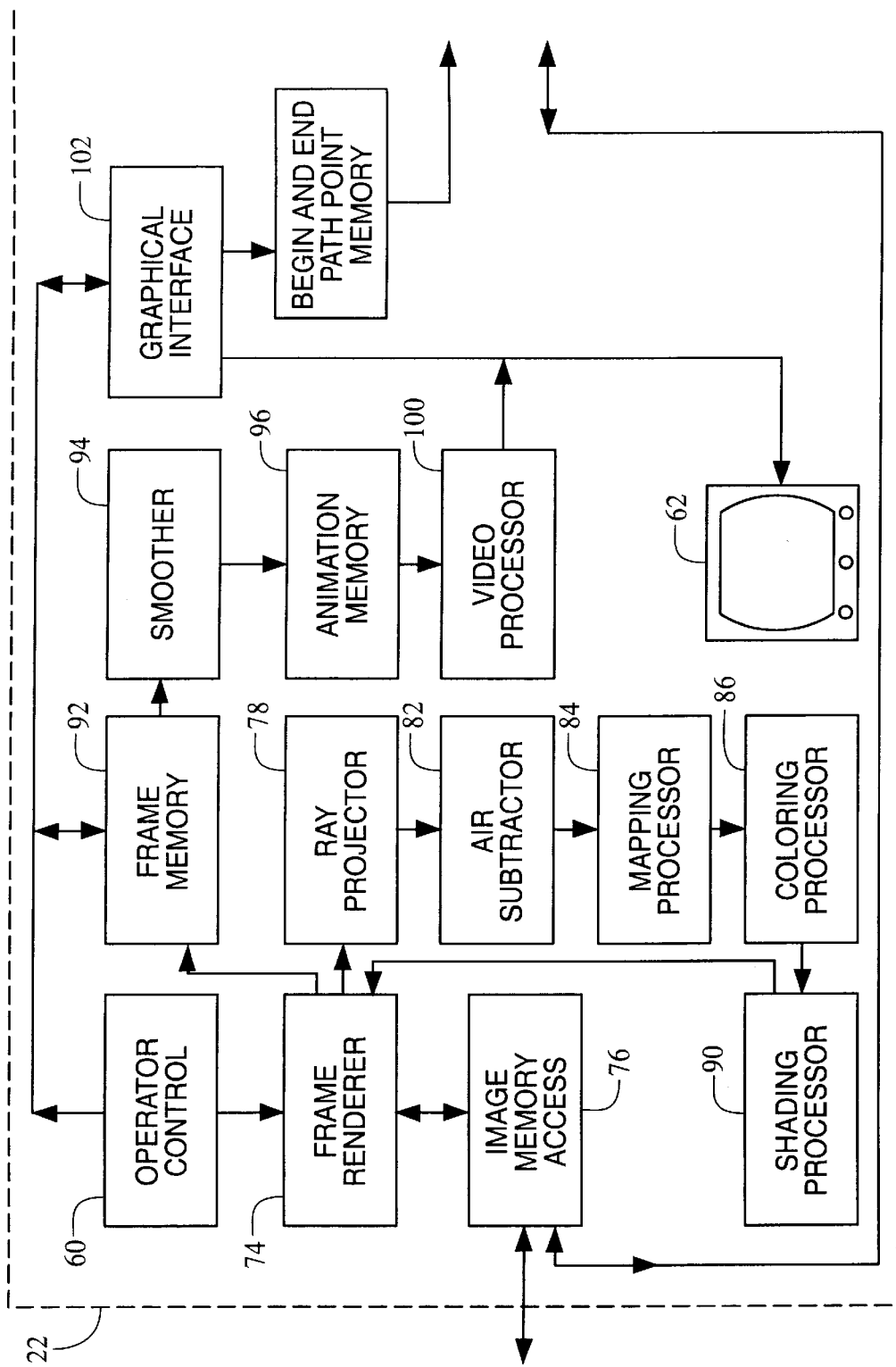
FIG. 2A and FIG. 2B are partial detailed diagrammatic illustrations comprising the whole of the sequence generating computer 22 of FIG. 1.

With continuing reference to FIG. 1 and reference to FIG. 2A, the sequence generating computer 22 includes an operator control 60 to be used by the human operator 24, typically, a radiologist, in order to select a desired path through an organ. The operator control 60 has the appropriate keys, joy stick, trackball, or mouse arrangement to permit the operator 24, to selectively access certain data in the volume image data memory 20 and cause it to be displayed on the screen of a sequence computer video display 62. This selection process is performed while viewing the CT data on the video display 62 in any of a number of formats such as slice images through the body, three-dimensional projections of external views of organs of interest, key-frame animation techniques and the like.

Figure 3:
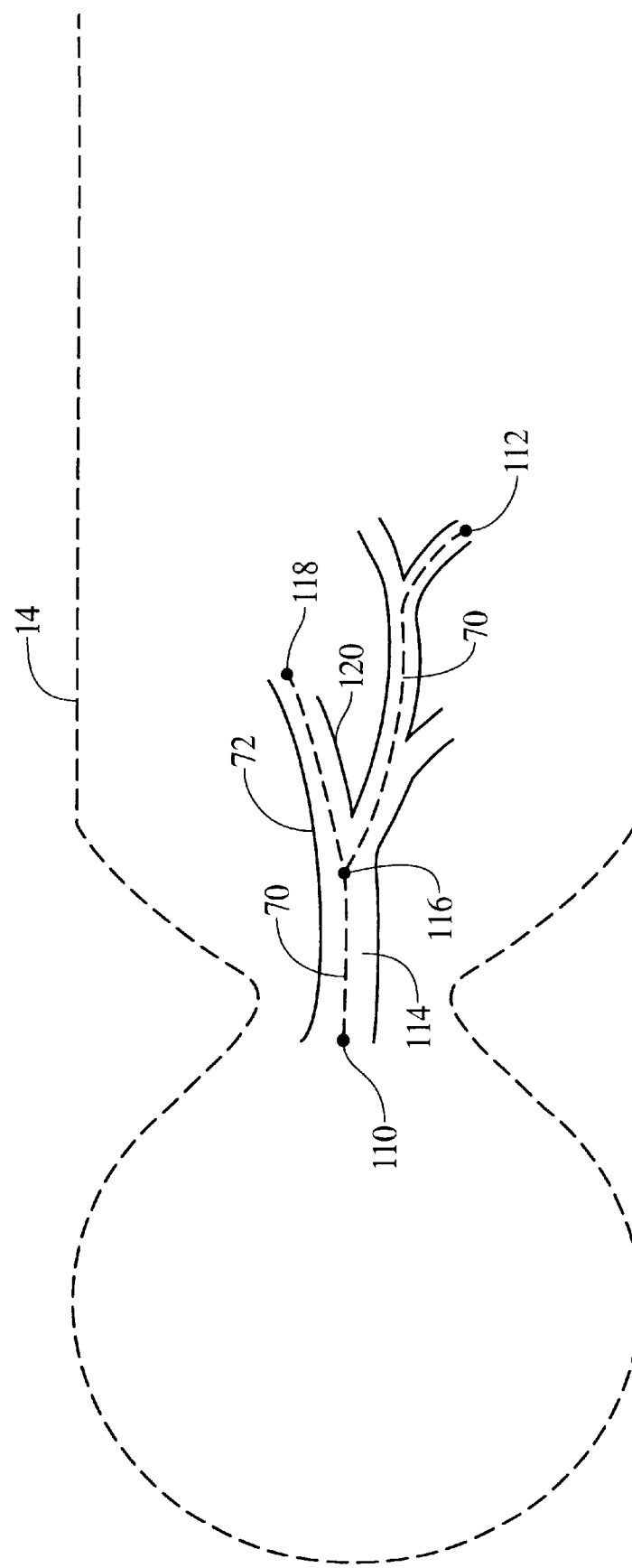
FIG. 3 is a diagrammatic illustration of the bronchial tubes of a patient which are to be viewed by interactive viewing system.

With continuing reference to FIG. 2A and reference to FIG. 3, in the preferred embodiment, the operator uses key-frame animation techniques to aid in the selection of a desired viewpath 70 in the bronchial tubes 72 of the patient 14. The illustrated example shows an external view of the patient and bronchial tubes. However, it is appreciated by those skilled in the art, that rather than an external view, internal views are generated by the key frame animation technique. Using the operator control 60, the operator or radiologist moves step-wise through the volumetric data to find the bronchial tubes. The operator inputs position and direction data into the operator control 60. The operator control 60 allows selection and adjustment of the field of view (FOV) of the key-frames as well other imaging parameters such as shading, coloring, and the like. A frame rendering processor 74 accesses certain data in the volume image data memory 20 by means of an image memory access processor 76. The frame rendering processor controls a ray projection processor 78 which calculates a plurality of rays from a viewing plane at the selected position and in the selected direction. The viewing plane is represented by the screen of the video terminal 62. The rays are projected from the viewing plane through the three-dimensional array of the volume data. The three-dimensional array data is characterized by grey scale values corresponding to each of a three-dimensional array of data points or voxels. The organs or tissues to be viewed are typically buried within the data. A ray from each pixel of the viewing or image plane is projected orthogonal to the viewing plane into the data. An air subtractor 82 subtracts or ignores pixels having the value of air along the calculated rays. The calculated rays continue until they either intersect a pixel indicative of a tissue or reach an endpoint of the three-dimensional array of data. From the depth at which each ray intersects a tissue and whether a ray intersects a tissue at all, a mapping processor 84 generates a map of the surface contour of the tissues when viewed from the viewing plane.

A coloring processor 86 adds color to the map depending on the grey scale level or CT value. This permits easier identification of certain tissues.

To give meaning to the surface contour, a shading processor or routine 90 adds shading to the exposed surfaces of the key-frame to give the effective depth in the direction perpendicular to the screen. The shading processor adds shading to the map of the surface contour as if a light source existed at the viewing plane. The shading processor uses any one of many methods for adding shading including depth shading, depth gradient shading, gray scale level gradient shading, and rendering with polygonal shapes.

Once each key frame images has been generated and suitably enhanced, it is stored in a key-frame memory 92. An optional smoother 94 generates a smooth path between sequential key frames. In the preferred embodiment, the smoother uses the technique of cubic splines. The sequence of smoothed key-frames are stored in an animation memory 96. A video processor 100 formats the data for display on the sequence computer video display 62.

Figure 4:
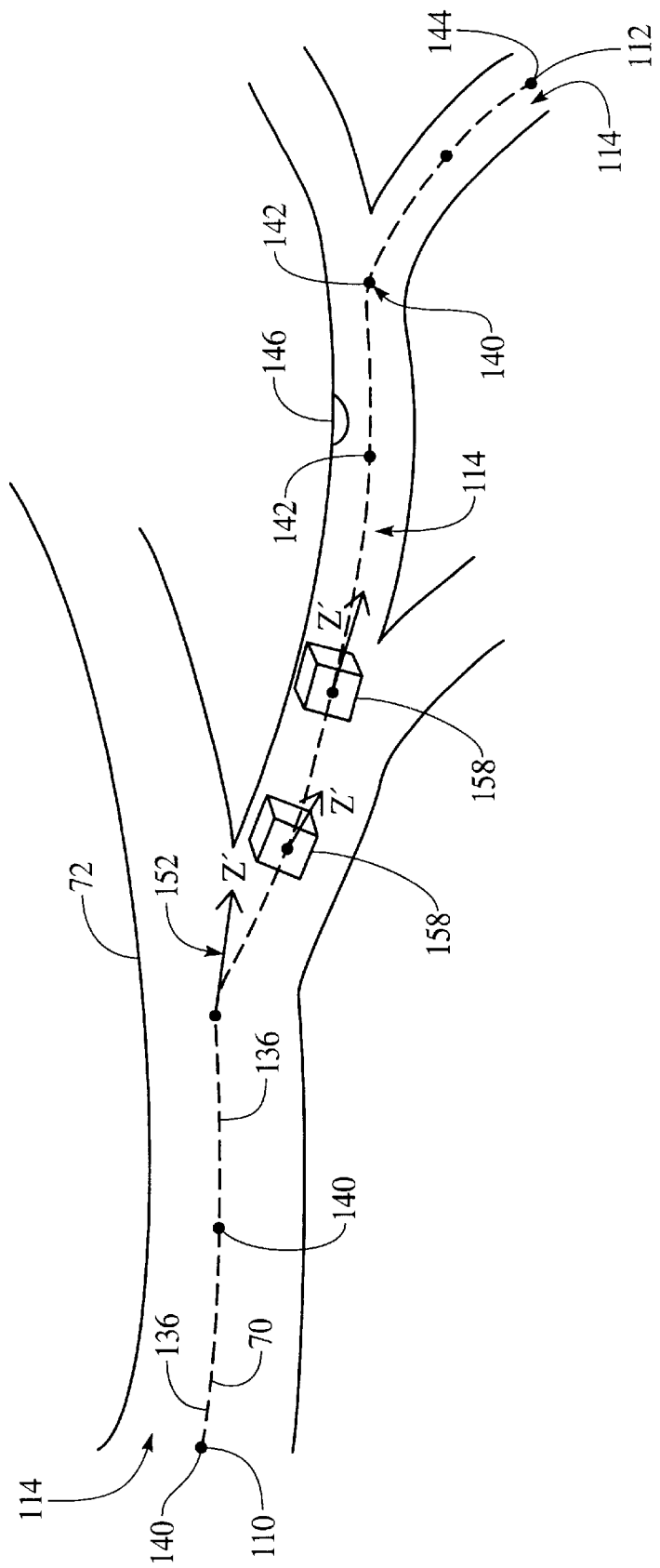
FIG. 4 is a enlarged view of the bronchial tubes of FIG. 3 showing in more detail a viewpath through the bronchial tubes.

With continuing reference to FIGS. 2A and 3, and further reference to FIG. 4, while viewing the key-frame images of the CT data on the video display 62, the operator selects the desired viewpath 70, via the operator control 60 and a graphical interface 102, by designating at least a beginning path point 110 and an end path point 112. In the example shown in FIG. 3, the operator selects a cavity or channel 114 within the bronchial tubes 72 between the epiglottis or beginning path point 110 and a point deep in the lung or the end path point 112. If desired, a second set of beginning and end path points 116, 118 may be selected to include a branch 120 within the organ. Additionally, the operator may mark or tag, via the operator control, certain tissue, such as a tumor 142, for easier identification by the remote viewer.

Figure 2B:
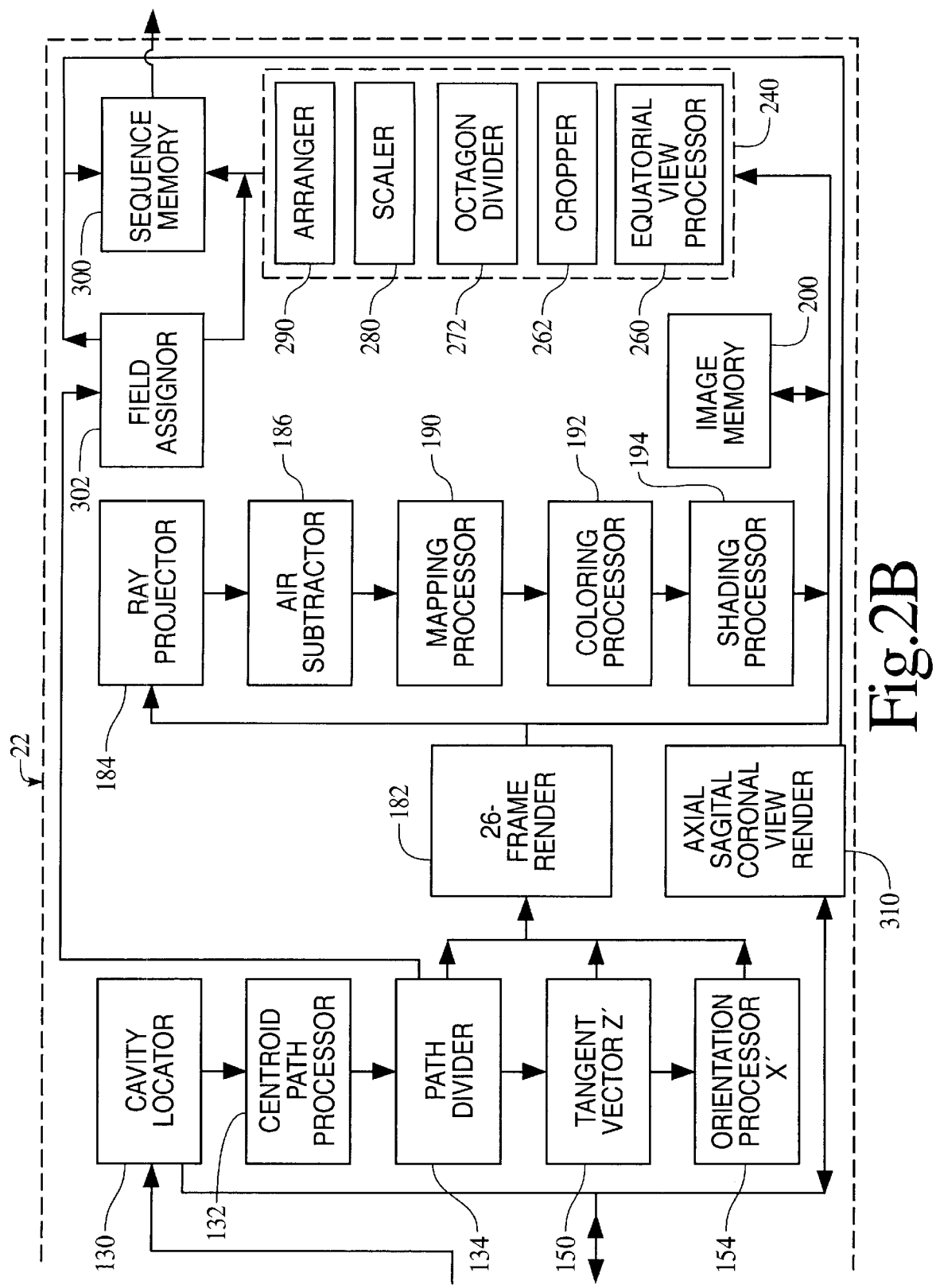

With continuing reference to FIG. 4 and reference to FIG. 2B, upon path selection, a cavity locator 130 scans the data between and around the path points 110, 112 to identify all CT pixel data having the image intensity, or Houndsfield value, of air which lies within the desired channel 114. In other embodiments, the cavity locator is programmed to scan for other uniform media that are in the desired cavities such as blood or cerebrospinal fluid. Based on the locus of pixels having the image intensity of air, a centroid path processor 132 calculates a centroid path generally midway in the channel. This centroid path has already been designated as the viewpath 70.

With continuing reference to FIG. 2B and FIG. 4, a path-dividing processor 134 divides the centroid path 70 into equal length segments 136. The length of the segments may be varied by the operator depending on the desired resolution of the final sequence. Endpoints of the segments 136 define viewpoints 140. These viewpoints are the central or vantage points of the spherical panoramic views that are to be generated.

In another embodiment, rather than allowing the path-dividing processor to define a multitude of viewpoints, the operator may selectively define one, two or more viewpoints for a sequence. For example, with reference to FIG. 4, by selecting only two viewpoints 142, the operator and remote viewer may focus the sequence or study on one area of concern, such as a tumor 146 in the bronchial tubes.

In the preferred embodiment of the present invention, the viewpoints 140 are low-distortion viewpoints. These low-distortion viewpoints 140 are to be the centers of spherical panoramic views generated from 26 flat images. In another embodiment of the invention, the viewpoints 140 are high-distortion viewpoints which are to be the centers of spherical panoramic views generated from only 6 flat images. Because more images are incorporated into the spherical panoramic views around low-distortion viewpoints, these viewpoints provide high-precision, high-detail examinations. In contradistinction, spherical images around high-distortion viewpoints do not provide as much precision or detail. Of course, the generation of 26-image spherical views requires significantly more computing power than the generation of 6-image spherical views.

Rendering

With continuing reference to FIG. 2B and FIG. 4, to ensure smooth transitions between each rendered spherical image, a tangent vector processor and associated memory 150 calculates and stores a tangential vector 152 to the viewpath 70 for each viewpoint. The tangential vector is defined as z'. For each successive viewpoint, an orientation processor and associated memory 154 defines and stores a vector x' which is orthogonal to z'. In FIG. 4, x' is directed orthogonal to the sheet. The orientation processor minimizes the angular deviation of the x' vectors between two neighboring viewpoints. With continuing reference to FIG. 4 and reference to FIGS. 5A and 5B, the z' and x' vectors define the orientation of the sets of 6 or 26 flat views 160, 162 that are to be generated. As an aid to this visualization, FIG. 4 shows cubes 158 where the front wall is defined by z' and the right side wall (with inexact perspective) is defined by x'. This process ensures that, during viewing, no two neighboring spherical images undergo a severe twist in orientation which could be perceived by the viewer as a shift in distortion when moving between the images.

In another embodiment, the tangential processor and orientation processor are absent from the system. In this embodiment, the x' and z' orientations of the 6 or 26 flat views simply mirror the x and z orientation of the stored volume data.

Figure 5B:
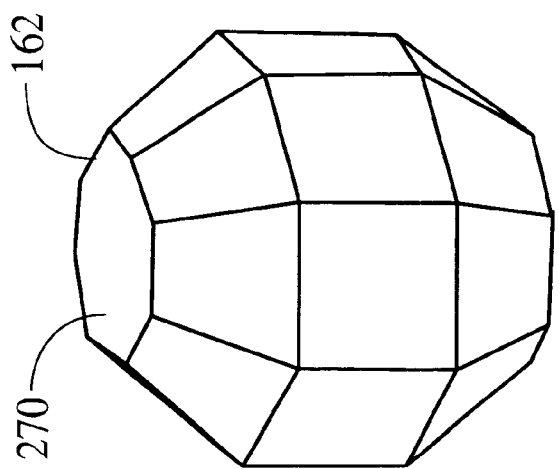
FIG. 5B is a diagrammatic illustration of an arrangement of 26 flat views to generate a low-distortion spherical image about viewpoint.
Figure 5A:
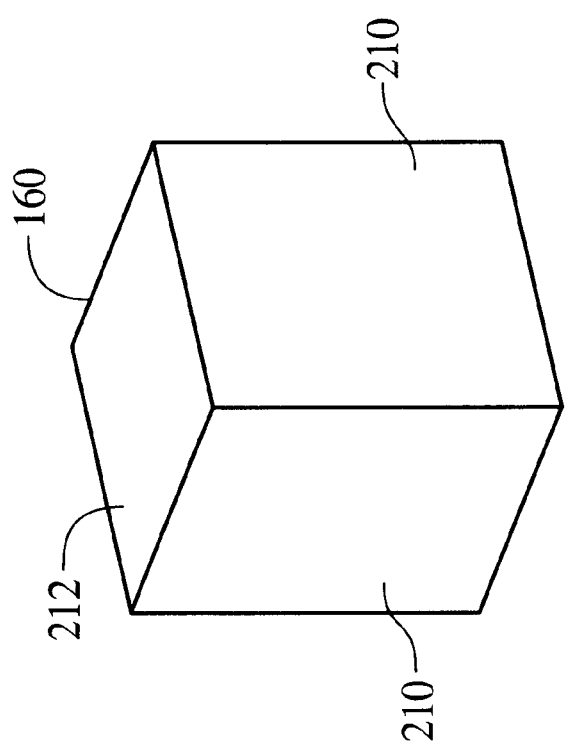
FIG. 5A is a diagrammatic illustration of an arrangement of six flat views to generate a high-distortion spherical image about viewpoint.

With continuing reference to FIGS. 5A and 5B, by way of background, an inherent limitation in creating spherical panoramic views is that the source images are flat, that is, the images are projections of a scene onto a plane. The panoramas created by flat images are therefore at best a multi-faceted sphere. A better approximation of the spherical panorama is achieved with smaller facets, or equivalently, source images with a smaller field of view (FOV). Using smaller facets, however, also increases the number of source images required to span the spherical view around a point. Further, the greater the number of source images, the greater is the amount of computer processing that is needed to create the spherical views.

As indicated above, the advantage of the 26-image spherical panorama is a more accurate approximation of the spherical world. As seen in FIGS. 5A and 5B, the 26-sided polygon 162 formed by the set of 26 images more closely approximates a sphere than the cube 160 formed by the set of 6 images. Accordingly, with continuing reference to FIGS. 2B and 5B, the sequence generating computer 22 creates a sequence of spherical panoramas using 26 source images per viewpoint.

Figure 6A:
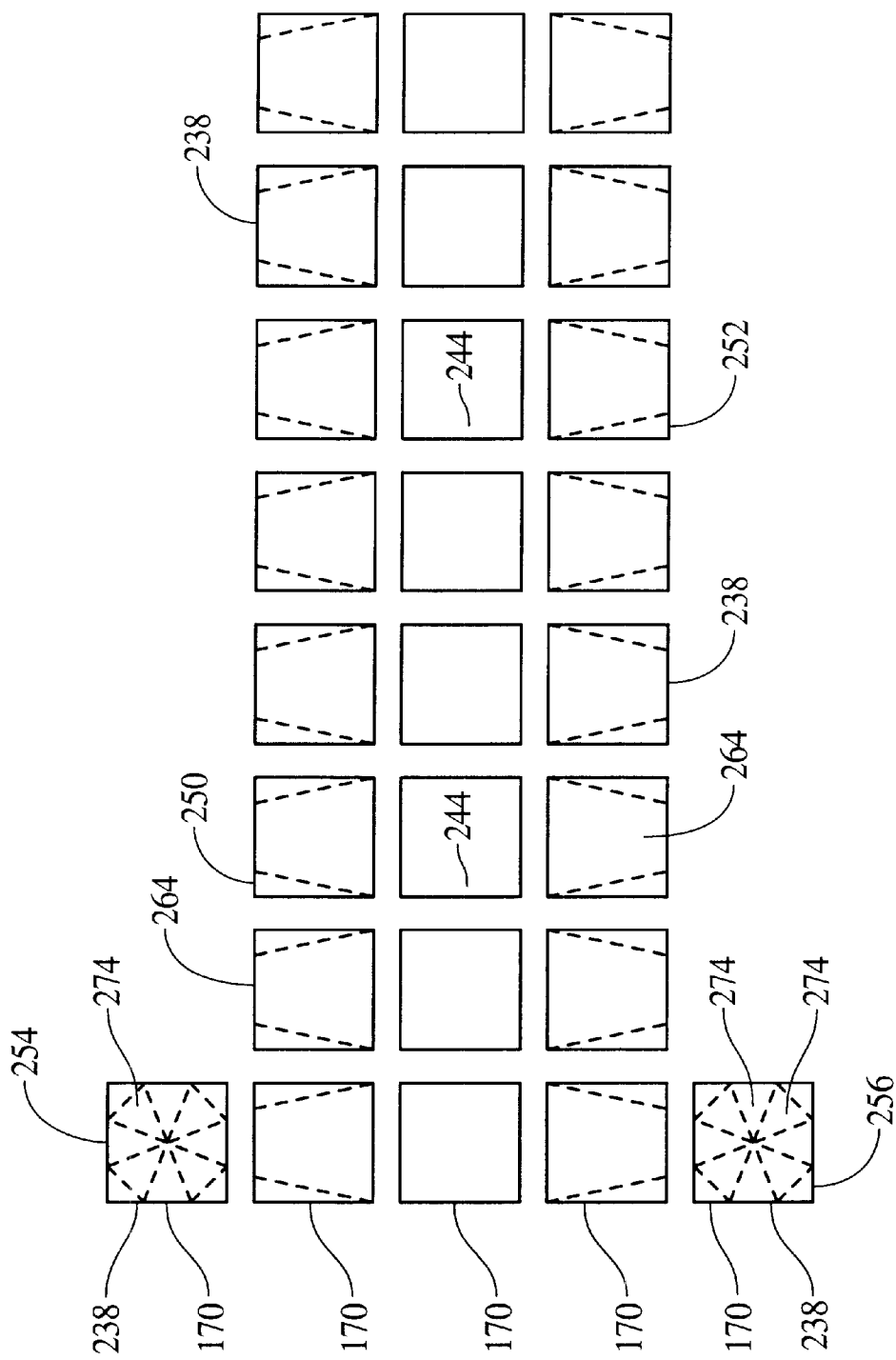
FIG. 6A illustrates the dividing and cropping of the 26 views of FIG. 5B to obtain a full, flat image for a low-distortion spherical panoramic view.
Figure 8:
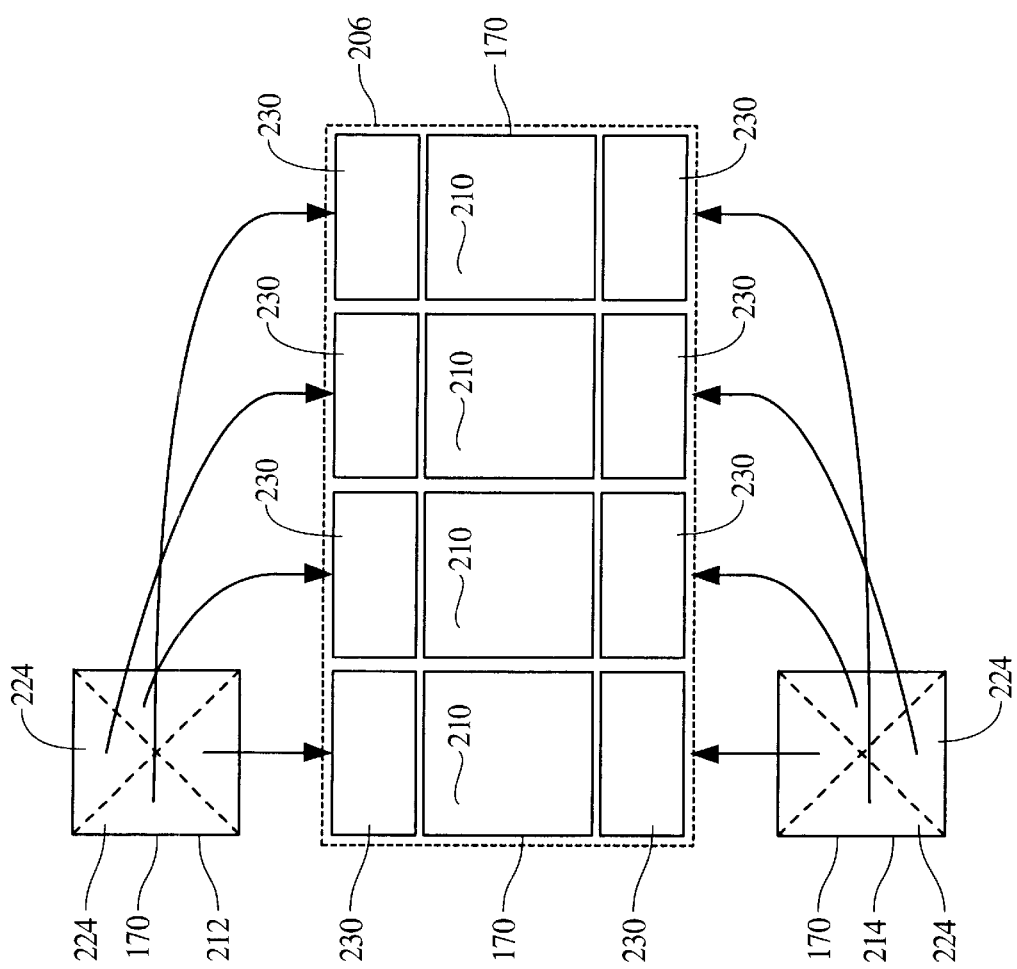
FIG. 8 illustrates the dividing and arrangement of the six views of FIG. 5A to obtain a full, flat image for a high-distortion spherical panoramic view.

With continuing reference to FIG. 5B, and reference to FIG. 6A and FIG. 8, source images 170 are acquired as square images with identical field of view along both horizontal and vertical directions. In the preferred embodiment, the pixel dimensions of the source images for the 26-face approach 162 are 256×256 and the FOV is 45.

With reference to FIG. 2B and FIG. 4, for every viewpoint 140, a 26-frame rendering processor 182 controls the rendering of 26 views around a viewpoint. With reference to FIG. 5B, each set of 26 views 162 covers the entire mappable space about a viewpoint. With reference to FIG. 2B, the rendering processor 182 controls a ray projection processor 184 which calculates a plurality of rays from a viewing plane at the selected viewpoint and in a direction dependent on the x' and y' vectors for the selected viewpoint. The rays are projected from the viewing plane through the three-dimensional array of the volume data. A ray from each pixel of the viewing or image plane is projected orthogonal to the viewing plane into the data.

During rendering of the set of 26 images, an air subtractor or routine 186 identifies those addressed pixels in the three-dimensional image volume which represent air or other selected tissue types which are not to be displayed. If the pixel value is representative of air, the ray projector 184 moves one pixel step in the projection direction, i.e., the direction perpendicular to the viewing screen, further into the image data and retrieves the next corresponding pixel. This pixel is again compared with the air or other preselected tissue values to determine whether it is to be displayed or not. This process is iteratively repeated until a memory cell or pixel value of the appropriate range to be displayed is located. From the depth at which each ray intersects a tissue and whether a ray intersects a tissue at all, a mapping processor 190 generates a map of the surface contour of the tissues when viewed from the viewing plane. It is to be appreciated by those skilled in the art that other tissue rendering techniques may be used in the present invention such as volumteric compositing and the like.

A coloring processor 192 adds color to the map depending on the grey scale level or CT value. This permits easier identification of certain tissues.

For a more lifelike or realistic three dimensional presentation, a shading processor or routine 194 provides shading values to each pixel. More specifically, an angle or position of illumination origination is defined. Rays are projected from the point of the illumination source to the defined volume, with the air or other selected tissue removed. The retrieved pixel value is made darker or lighter in accordance with the distance and surface tangent relative to the light source. Surfaces which are obstructed from the light source by other surfaces are shaded most darkly. The degree of shading which is added may be selectively adjustable from the operator control which can be conceptualized as brightening or darkening the illumination source. Similarly, the illumination source can be repositioned and the shading process repeated in order to illustrate other parts of the displayed object better. In the preferred embodiment, the illumination source is at the viewing plane of each rendered flat image. Each rendered image stored in an image memory 200.

Compositing

With continuing reference to FIG. 2B, and reference to FIGURES GA and GB, after a set of 26 square, flat, partial images 238 is created, a compositing processor 240 crops, scales and combines the set of partial images to create a full, flat, output image 242 which represents a spherical panoramic view. The special compositing technique employed by the compositing processor increases resolution and decreases distortion in the resultant spherical panoramic image.

The composited, full, flat, output image 242 is similar in nature to a rectangular world map of the earth. Of the set of 26 partial images 238, eight equatorial faces or partial images 244 form the equator of the spherical image. With reference to FIG. 6A, above and below the equatorial faces are eight northern hemispherical faces 250 and eight southern hemispherical faces 252. A top or northern pole face 254 and a bottom or southern pole face 256 completes the 26-sided spherical approximation.

With reference to FIGS. 2B, GA and 6B, an equatorial view processor or routine 260 places the 8 equatorial views 244 side by side forming the middle portion of the full output image 242. To appropriately size the partial images to form the 26-sided sphere, a cropping processor 262 crops (at the dotted lines of FIG. 7A) the northern and southern hemispherical faces 250, 252 into trapezoidal shapes 264 (with sides represented by dotted lines). Further, the cropping processor 262 crops the top and bottom faces 254, 256 into an octagonal shape 270 (of FIG. 5B). A octagonal view divider 272 splits the octagonal faces 270 into eight triangles 274 such that each side of the octagons 270 is the base of a triangle 274.

A scaling processor 280 scales the northern and southern hemispherical trapezoidally cropped views 264 into 256× 256 pixel rectangles 282. Further, the scaling processor 280 scales each triangle 270 of the octagonal views 270 into 256×128 pixel rectangles 286. To achieve these transformations, the scaling processor inserts additional interpolated data between selected data points to fill out the trapezoidal and triangular arrays and transform them into rectangular arrays. In the preferred embodiment, the scaling processor uses the technique of cubic interpolation. However, it is to be appreciated that other interpolation techniques may be used. An arranger 290 appropriately places the scaled triangles above and below the cropped and scaled hemispherical faces 282. Optionally, the arranging processor averages data in the overlapped edges. The resultant full, flat images from the compositor 240 are stored in a sequence memory 300. In the preferred embodiment, the composited, full image is an array of 2048×1024 pixel data points.

In the preferred embodiment, the full, flat images comply with the DICOM (Digital Imaging and Communications in Medicine) standard used by most hospitals. However, it is to be appreciated that the image data may be conformed to other imaging standards.

A field processor 302 assigns spatial information to each of the generated full images to assist in the later ordering and display of the images. Optionally, if the operator marks or tags a specific tissue, such as a tumor, the field processor may associate the three-dimensional coordinate of the tissue with the sequence of images. The entire sequence of images and associated fields containing spatial and other information is stored in the sequence memory 300.

The sequence of full views provides advantages not seen in the prior art. As contrasted with key-frame based animation, there is no need to constantly reorient oneself for capture of views not forward-facing along the path. Further, the back faces or surfaces of tumors or other structures are naturally rendered as part of the spherical views permitting easy capture and inspection of such views.

Figure 7:
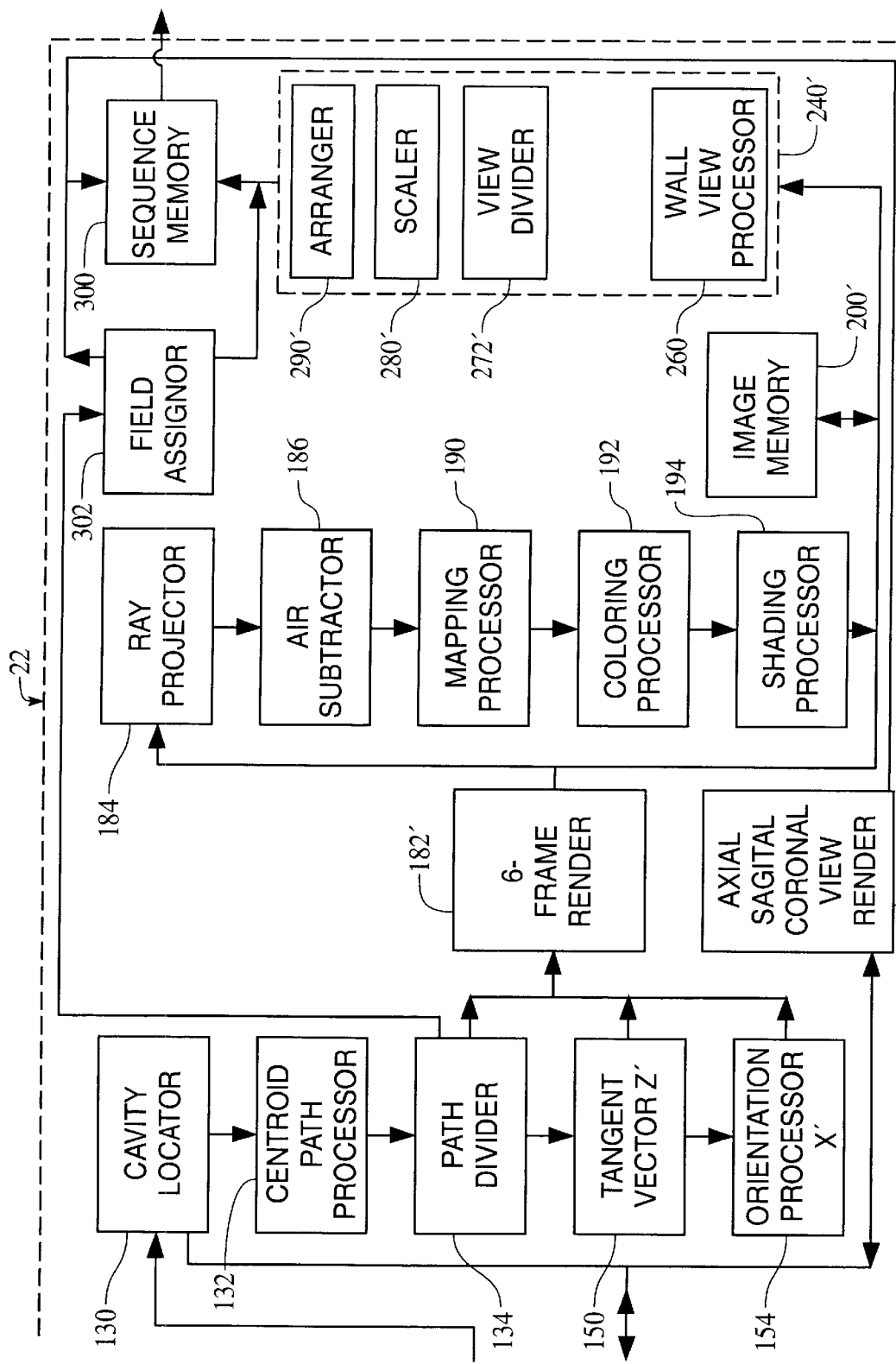

In another embodiment of the invention, the sequence generating computer creates full, flat images from 6 views about each viewpoint. These viewpoints are considered high-distortion viewpoints. With reference to FIGS. 5A, 7 and 8, the sequence generating computer 22 acquires six source images 170 for each viewpoint. The advantage of this strategy is lesser computer processing time. The source images 170 are acquired as square images with identical field of view along both horizontal and vertical directions. The FOV and the pixel dimensions of the source images for the 6-face approach 160 are 90 and 512×512, respectively.

With continuing reference to FIG. 7 (in which elements identical to those in FIG. 2B are shown with the same reference numerals, and in which elements analogous to those in FIG. 2B are shown with the same but primed (') reference numerals) and reference to FIG. 4, for every viewpoint 140, a 6-frame rendering processor 182' controls the rendering of 6 views about each viewpoint. With reference to FIG. 5A, each set of 6 views 160 covers the entire mappable space about a viewpoint. With continuing reference to FIG. 7, the rendering processor 182' control a ray projection processor 184. During rendering of the 6-image set, an air subtractor or routine 186 identifies those addressed pixels in the three-dimensional image volume which represent air or other selected tissue types which are not to be displayed. From the depth at which each ray intersects a desired tissue and whether a ray intersects a tissue at all, a mapping processor 190 generates a map of the surface contour of the tissues when viewed from the viewing plane. A coloring processor 192 adds color to the map depending on the grey scale level or CT value. A shading processor or routine 194 provides shading values to each pixel. Each image and set of 6 images are stored in an image memory 200'.

With continuing reference to FIG. 7 and reference to FIG. 8, after a set of 6 flat square views 170 are created, a compositing processor 240' combines the set of square images to create a full, flat, output image 206 which represents a spherical panoramic view. The composited image is similar in nature to a rectangular world map of the earth.

With reference to FIGS. 5A and 8, the six flat, square views are analogous to a cubic room which has four wall views 210, a ceiling view 212 and a floor view 214. With continuing reference to FIGS. 5A and 8 and reference to FIG. 7, a wall processor or routine 260' places the four wall views 210 side by side to form the middle portion of the full output image 206. A view dividing processor 272' divides the ceiling view 212 and floor view 214 into four triangles 224 each. Of course, each triangle of the ceiling and floor views is associated with the wall to which its base, when viewed as the cubic set of six images, is adjacent. A scaling processor 280' scales each triangle into a rectangular array of 512×256 pixels 230. To achieve this transformation, the scaling processor inserts additional interpolated data between selected data points to fill out the triangular array and transform it into a rectangular array. An arranging processor 290' appropriately aligns and/or overlaps the edges of the wall views 210 and the ceiling and floor views 212, 214 to form the final output image 206. The arranging processor averages the data in the overlapped edges. The composited, full image is an array of 2048×1024 pixel data points.

A field processor 302 assigns spatial information to each of the generated full images to assist in the later ordering and display of the images. The entire sequence of images and associated fields containing spatial information is stored in the sequence memory 300.

Additional Views

Returning to the embodiment described in FIG. 2B, to provide the remote viewer with visio-spatial context an additional view rendering processor 310 renders axial, sagittal and coronal views of any of the entire body, portion of the body, external three-dimensional view of the organ of interest or any other r desired view. These views are to be displayed alongside a spherical image on the remote video terminal.

The field assignor 302 assigns spatial information to the views to permit them to be coordinated with the spherical panoramic images. The views are then stored in the sequence memory 300.

Transfer and Display

Figure 2C:
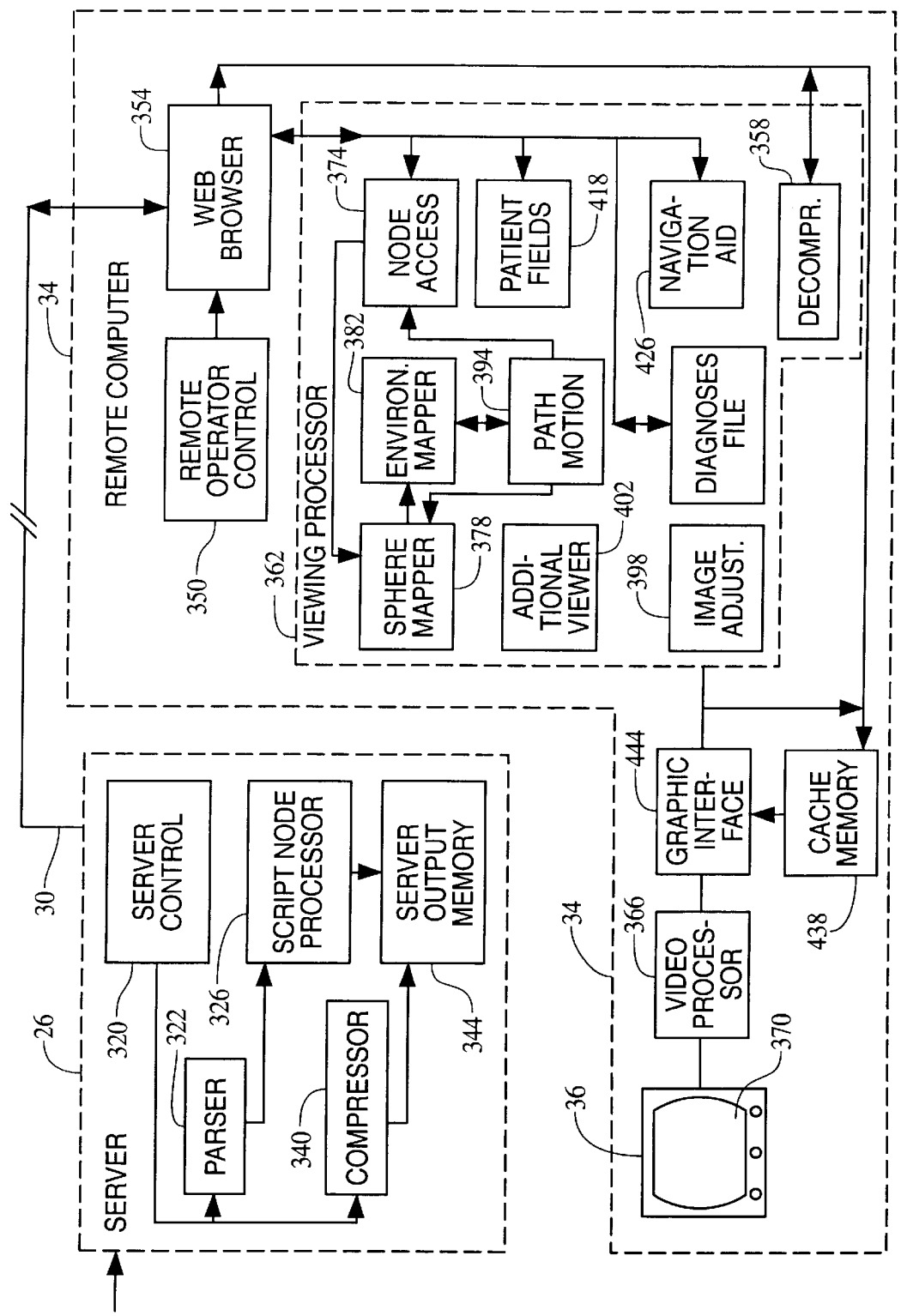
FIG. 2C is a full diagrammatic illustration of the server 22 and remote computer 34 of FIG. 1.

With reference to FIG. 1 and FIG. 2C, to make the sequence available over the network 30 the data from the sequence memory is transferred to the designated server 26. In the preferred embodiment, the server supports a local area network in a hospital and is accordingly DICOM compliant. However, it is to be appreciated that the server could also support a wide area network including the World Wide Web. Further, it is to be appreciated that data protocols other than DICOM may be used with the present invention.

With continuing reference to FIG. 2C, upon reception of the sequence data from the sequence memory 300, a server control 320 directs a parsing processor 322 to parse the spatial information fields associated with the sequence of full images as well as the axial, coronal and sagittal images. Based on the results of the parsing, a script node processor 326 creates a single script file containing all spatial and linking information for the sequence of full images as well as the associated axial, sagittal and coronal views. In the preferred embodiment, this script file is compliant with VMRL 2.0 (Virtual Reality Modeling Language) for viewing with a spherical viewer application.

Although it is possible to link the display of one spherical image to another via a simple URL (Uniform Resource Locator) link, this is undesirable because the download and parsing of each text file takes a significant amount of time. Consequently, it takes a significant amount of time to display an image. Once an image has been viewed, it and its script file are cached on a hard disk of the remote computer system. However, to review the image, the script file must be re-parsed. Parsing time depends on processor speed, random access memory and the text file size and may take from ten to sixty seconds.

The server control 320 also directs a compression processor 340 to parametrically compress each of the spherical images. In the preferred embodiment, the compression processor compresses the data into JPEG files with an 8 to 1 ratio. However, in other embodiments, compressed and non-compressed files, such as BMP and GIF, and other compression ratios are used which may depend on the capabilities of the system and the acceptable level of distortion caused by compression-decompression. The compressed images and the script file are stored in a server output memory 344.

Parsing and compression of the virtual endoscopy sequence permits more rapid transmission of the data over networks and more efficient use of network resources. However, as bandwidth widens and network resources improve, it is contemplated that compression of the data and indeed the server may be omitted in some viewing systems.

The data in the server output memory 344 is made available to a plurality of remote computers 34 via the local area network 30. The remote viewer 32 inputs commands to the remote computer 34 to call up the desired virtual endoscopy sequence. The commands are entered to a remote operator control 350 which includes a keyboard and trackball. It is to be appreciated that other input devices may be used such as a joystick, a mouse, a touchpad and the like. A web browser Java applet, processor or application 354 on the remote computer accesses the script file in the server output memory 344 and downloads it to a hard drive or cache memory 438 on the remote computer. Typically, the address of the script file is embedded in another text page with an .html (hypertext modeling language) file extension. When the page is opened in the web browser Java applet 354, the applet launches a virtual reality viewing processor or application 362. The viewer application 362 then begins the downloading of the compressed full images of the sequence. The viewer application includes a decompressing processor or routine 358 to expand the compressed full image files.

Figure 9:
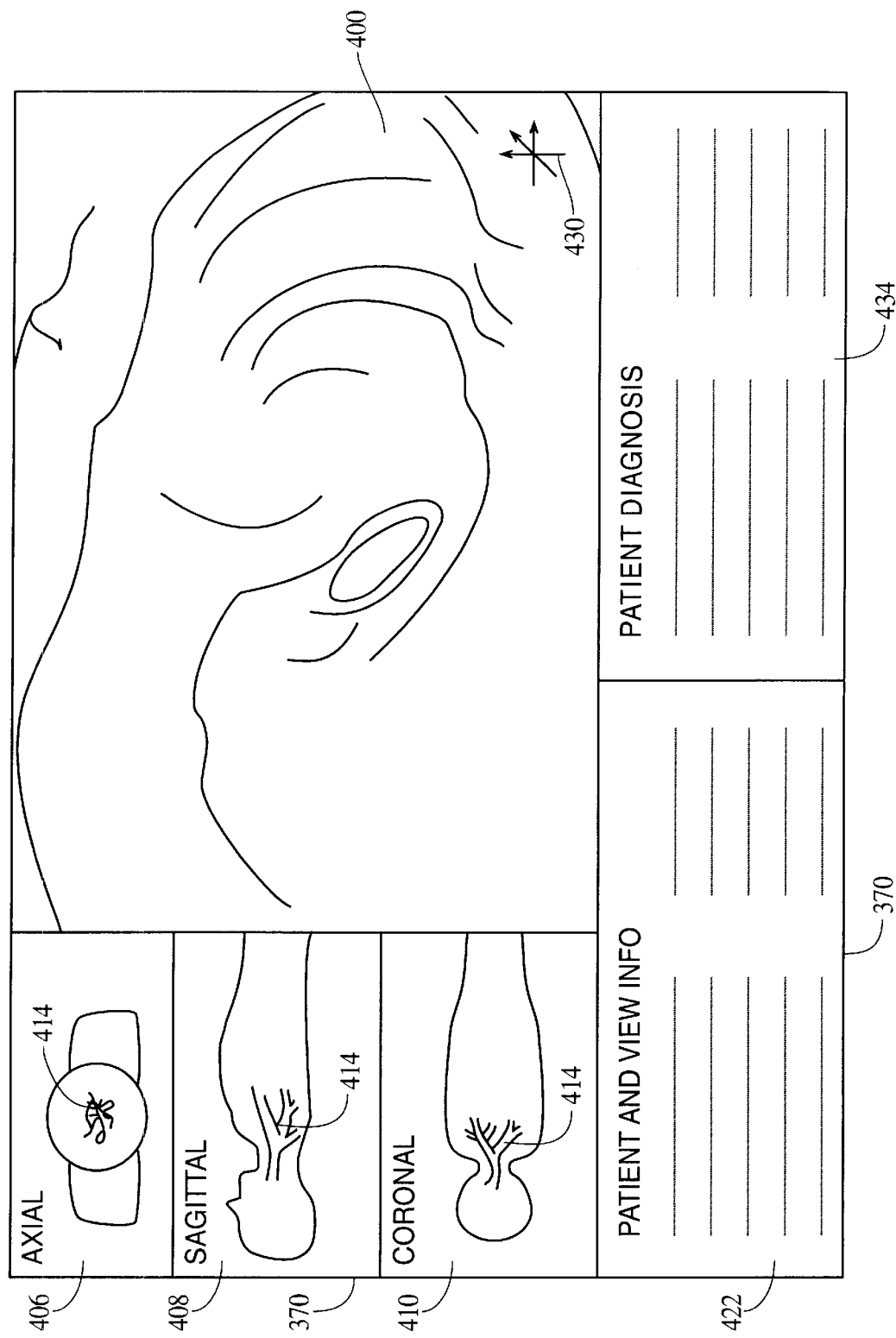
FIG. 9 is a diagrammatic illustration of a representative display of the spherical image, the axial, sagittal and coronal views associated with the image, patient and view information, and patient diagnoses fields that is displayed on the display monitor 36 of FIG. 1.

A video processor 366 displays the images on the video screen 370 (see also FIG. 9). The viewer application 362 permits the viewing of the entire visual space from each viewpoint of the sequence. It is to be appreciated that other browsers or applications may be used in conjunction with more limited views of visual space, such as cylindrical views. The viewer application 362 includes a node accessing processor or routine 374 to access a selected node or viewpoint and the full, flat image associated therewith. A sphere-mapping processor 378 maps the flat image into a 360×180 degree spherical panorama.

The viewing application or processor 362 supports two rotational degrees of freedom: pitch and yaw. Pitch and yaw are controlled by an environment mapping processor 382 which alters the mapping of the displayed environment. In this process, the panorama is re-projected onto the spheric surface surrounding the remote viewer thereby displaying unseen portions of the spherical image. Taking the plane of the screen 370 of the monitor 36 as a reference origin, the remote operator control 350 and viewing application 362 enable the remote viewer to rotate pitch and yaw to selectively view any portion of the spherical image about its viewpoint.

The operator control 350 and viewing application 362 permit the remote viewer to move along the viewpath in a forward or backward direction while selecting the viewing direction. This provides unique viewing techniques such as panning down the wall of the bronchial tube while looking directly at the wall. This is not possible with forward-looking techniques where the viewer obtains only a peripheral view of the wall.

To provide movement along the viewpath, a path motion processor 394 scales or translates the displayed view. For example, when the viewer is looking forward while moving forward along the viewpath, the path motion processor enlarges the scale of the forward view, i.e., zooms in, to give the illusion that the viewer is moving forward. Analogously, when the viewer is looking forward while moving backward, the path motion processor reduces the scale of the forward view to give the illusion that the viewer is moving backward. To give the illusion of moving forward along the viewpath while looking sideways, the path motion processor translates image data from the side of the displayed portion of the full image onto the screen and alters the mapping of the displayed view. When movement along the path reaches the limits of the displayed spherical view, the path motion processor triggers the display of the next spherical view.

In addition, the remote operator control 350 and viewing application 362 allow the remote viewer, by means of an image adjusting processor or routine 398 to adjust the image parameters such as field of view (i.e., zoom in and out), and the like. As the remote viewer redirects or otherwise changes the view, the video processor 366 continues to cause the video display 36 to display a three dimensional presentation of the interior of the cavity onto the screen.

With continuing reference to FIG. 2C and reference to FIG. 9, the viewing processor 362 directs the display of the sphere-mapped image 400 onto the screen 370. An additional view processor or routine 402 in the viewer application 362 provides display of an axial, a sagittal, and a coronal view 406, 408, 410 of the silhouette of the patient and of an external view of the bronchial tubes or organ of interest. In other embodiments, the additional view processor supports the display of orthogonal views of the patient or a region of the patient such as a silhouette of the patient, an external view of the organ of interest, slice images through the body, and the like. The additional view processor incorporates an indicator 414 onto each of the additional views 406, 408, 410 to dynamically show the location and orientation of the viewpoint of the correspondingly displayed spherical image 400. In the preferred embodiment the indicator has green cross-hairs which indicate the location of the viewpoint. A red dot shows the viewing direction by revolving about the center of the cross-hairs in correspondence with the view direction. The red dot stops within one of the quadrants formed by the cross-hairs to show the angular viewing direction within the plane of the additional view.

A patient field processor or routine 418 in the viewer application provides the display of patient text and view information fields 422 for accurate presentation of study data. A navigation aid processor 426 displays an orientation pointer 430 in the display of the spherical image 400. The orientation pointer is a visual aid for interpretation of the context of the image data. Optionally, the viewer application permits a remote viewer, such as radiologist or disease specialist, to view and enter diagnostic opinions or other annotations into a patient diagnoses data file 434 for association with the images and the sequence. Other remote viewers accessing the server would then be able to view the annotations associated with the images. To assist the remote viewers in quickly locating particular annotations, the viewer application supports an option to find or jump to a selected word, number or alphanumeric combination, or position and viewer orientation in the sequence of images or study.

Viewed images are stored in the cache memory 438 for more easy retrieval should the viewer choose to move backwards in the sequence. A graphical interface 444 permits simultaneous display and exchange of data between the output of the viewing processor and the input of the remote viewer.

Viewers of the sequence of spherical images have the liberty to turn at will and view in any direction from a particular viewpoint instead of being constrained to a pre-determined look-forward path. In this way, viewers retain the sense of order and space which a look-forward series provides but with the added capability to investigate completely a space from any given viewpoint. Further, the viewers employ an intuitive interface (point and click) instead of a frustrating and time consuming play-reverse-replay interface as with to video.

The sequence of spherical images of the present invention is selectively downloaded as needed, image by image. This enables more productive use of network time by radiologists in contradistinction to traditional video for which an entire sequence is downloaded before being viewed.

The invention has been described with reference to the preferred embodiments. obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of generating a three dimensional image presentation using a computer comprising:
   a) storing image data indicative of a three dimensional array of pixels;
   b) selecting a viewpoint within the three-dimensional array;
   c) generating six two-dimensional arrays which in total cover the entire spherical space about the viewpoint;
   d) dividing at least one of the plurality of two-dimensional arrays into a plurality of first polygon arrays, the first polygon arrays being triangular arrays;
   e) scaling the plurality of first polygon arrays into a Plurality of second polygon arrays, the second polygon arrays being rectangular arrays;
   f) combining the plurality of second polygon arrays and a portion of the plurality of two-dimensional arrays to form a full two-dimensional array covering the entire spherical space about the viewpoint;
   g) mapping the full two-dimensional array into a spherical view; and,
   h) displaying at least a portion of the mapped, full, two-dimensional array as image pixels in a human-readable display.

2. The method as set forth in claim 1 further including determining an angle of a surface corresponding to each image pixel value of at least one of the two-dimensional arrays and altering the brightness of each pixel in accordance with the surface angle.

3. The method as set forth in claim 1 wherein the step of generating a plurality of two-dimensional arrays which in total cover the entire spherical space about the viewpoint includes:
   comparing each pixel value of at least one of the two-dimensional arrays with a threshold criteria;
   in response to a pixel value failing to meet the threshold criteria, projecting deeper into the image data until a pixel value that meets the threshold criteria is identified; and,
   inserting the pixel value that meets the threshold criteria into the two-dimensional array.

4. The method as set forth in claim 1 further including the steps of:
   generating a separate two-dimensional array from the three dimensional array of image data, the separate two-dimensional array intersecting the spherical view;
   displaying the separate two-dimensional array on the human-readable display.

5. The method as set forth in claim 4 further including the step of:
   indicating the location of the viewpoint on the separate two-dimensional array of an area around the full, two-dimensional array.

6. The method as set forth in claim 1 wherein the step of displaying includes selectively displaying only a portion of the full two-dimensional array.

7. The method as set forth in claim 1 further including storing the full two-dimensional array on a server to provide remote access over a network and remote display on the human-readable display.

8. A method of generating a three dimensional image presentation using a computer comprising:
   a) storing image data indicative of a three dimensional array of pixels;
   b) selecting a viewpoint within the three-dimensional array;
   c) generating a plurality of two-dimensional arrays which in total cover the entire spherical space about the viewpoint;
   d) dividing at least one of the plurality of two-dimensional arrays into a plurality of first polygon arrays;
   e) scaling the plurality of first polygon arrays into a plurality of second polygon arrays;
   f) cropping at least one of the plurality of the two-dimensional arrays into a third polygon array;
   g) scaling the third polygon array into a fourth polygon array;
   h) combining the plurality of second polygon arrays, a portion of the plurality of two-dimensional arrays and the fourth polygon array to form a full two-dimensional array covering the entire spherical space about the viewpoint;
   i) mapping the full two-dimensional array into a spherical view; and,
   j) displaying at least a portion of the mapped, full, two-dimensional array as image pixels in a human-readable display.

9. The method as set forth in claim 8 further including generating the three dimensional array of pixels through a medical diagnostic exam of a patient.

10. The method as set forth in claim 8 wherein the third polygon array is a trapezoidal array.

11. The method as set forth in claim 8 further including selectively increasing and decreasing the value of a portion of the two-dimensional arrays to create the appearance of shading.

* * * * *